US011806477B1

(12) United States Patent
Adams (10) Patent No.: US 11,806,477 B1
(45) Date of Patent: Nov. 7, 2023

(54) CONDUIT HOLDING DEVICE

(71) Applicant: Justin Adams, Oakdale, CA (US)

(72) Inventor: Justin Adams, Oakdale, CA (US)

( * ) Notice: Subject to any disclaimer, the term of this patent is extended or adjusted under 35 U.S.C. 154(b) by 22 days.

(21) Appl. No.: 17/808,658

(22) Filed: Jun. 24, 2022

(51) Int. Cl.
*A61M 16/08* (2006.01)
*A61G 7/05* (2006.01)

(52) U.S. Cl.
CPC ....... *A61M 16/0875* (2013.01); *A61G 7/0503* (2013.01); *A61M 2209/082* (2013.01)

(58) Field of Classification Search
CPC ........ A61M 16/0875; A61M 2209/082; A61G 7/0503
See application file for complete search history.

(56) References Cited

U.S. PATENT DOCUMENTS

| | | | |
|---|---|---|---|
| 2,718,886 A | 9/1955 | Sutton | |
| 3,338,538 A | 8/1967 | Roche | |
| 3,530,515 A * | 9/1970 | Jacoby | A61G 7/0501 128/200.24 |
| 5,109,736 A | 5/1992 | Dixon | |
| 6,971,617 B2 * | 12/2005 | Nguyen | F16M 11/045 211/172 |
| 8,191,551 B2 | 6/2012 | Skovgard | |
| 8,540,196 B1 | 9/2013 | Hodson | |
| 9,433,736 B2 | 9/2016 | Smith | |
| 10,422,445 B2 | 9/2019 | Butcher | |
| 10,716,726 B2 * | 7/2020 | Bergman | A61G 13/101 |
| 10,773,035 B2 | 9/2020 | Klinger | |
| 11,118,704 B2 | 9/2021 | Gill | |
| 2007/0045481 A1 * | 3/2007 | Adams | A61G 7/0503 248/59 |
| 2015/0238377 A1 * | 8/2015 | Muhammad | F16B 2/10 248/68.1 |
| 2016/0270995 A1 * | 9/2016 | Carter | A61G 13/10 |
| 2017/0197050 A1 * | 7/2017 | Reinburg | F16M 11/06 |

OTHER PUBLICATIONS

NPL—Cite No. 1—Website available at least as early as Nov. 9, 2020 at: https://www.thingiverse.com/thing:4673962.

* cited by examiner

*Primary Examiner* — Anita M King
(74) *Attorney, Agent, or Firm* — PATENTFILE, LLC; Bradley C. Fach; Steven R. Kick (57) ABSTRACT

A conduit holding device may include a mounting mechanism having a fixed plate, and optionally, a movable plate that may be movable towards and away from the fixed plate. A rail may be coupled to the mounting mechanism, the rail having a first end, a second end, an elongated front side, and an opposing elongated back side. A platform may be movably coupled to the rail so that the platform may be repositionable between the first second ends. The platform may have one or more front conveyances and back conveyances. The platform may be movably coupled to the rail with a front conveyance in contact with the front side of the rail and with a back conveyance in contact with the back side of the rail. A clamp may be coupled to the platform, and the clamp may be configured to arrest a first portion of a conduit to the platform.

20 Claims, 7 Drawing Sheets

CONDUIT HOLDING DEVICE

FIELD OF THE INVENTION

This patent specification relates to the field of conduit holding and securing devices. More specifically, this patent specification relates to a conduit holding device which enables a continuous positive airway pressure (CPAP) machine conduit that is engaged to a user to be easily repositioned and suspended above the user while also enabling the device to be secured to a plurality of objects.

BACKGROUND

Continuous positive airway pressure (CPAP) machines typically use a breathing tube or conduit to supply pressurized air to a mask which is connected to the user's nose or mouth. User movement during sleep can cause separation between the mask and the user, reducing the effectiveness of CPAP treatment. CPAP tube holders help to keep CPAP tubing suspended above the user which minimizes the risk of the hose becoming dislodged or getting pulled or pinched during sleep, maximizing the effectiveness of the CPAP treatment. Additionally, CPAP tube holders provide the user more comfort as they reduce the amount of pull that the CPAP tubing exerts on the user's mask. Currently available CPAP tube holders either don't provide the user enough range of motion or have a high vertical profile which is cumbersome and visually unappealing.

Therefore, a need exists for novel CPAP tube and conduit holders. A further need exists for novel CPAP tube and conduit holders which are configured to reduce the amount of pull that the CPAP tubing exerts on the user's mask while also providing the user enough range of motion and a low-profile form factor.

BRIEF SUMMARY OF THE INVENTION

A conduit holding device is provided which provides a mechanism for conduit or tube movement with range of motion along the x-axis with a low vertical profile and effective tube concealment area behind objects, such as a user's headboard. The device includes a sliding platform that allows the conduit or tubing supported by the device to move with the user, providing greater range of movement than a static tube holder alone can provide with the additional benefit of a low vertical profile which provides a method for better concealment of CPAP tubing and other types of tubing or conduit.

In some embodiments, the device may include a rail having a first end, a second end, an elongated front side, and an opposing elongated back side. A mounting mechanism may be coupled to the rail, and the mounting mechanism may have a fixed plate and a fixed plate extension. The fixed plate extension may couple the fixed plate to the rail, and the fixed plate may have one or more fastener apertures which may be configured to receive a device fastener. The one or more device fasteners may be used to couple the fixed plate to an object, such as a wall, headboard, etc. A platform may be movably coupled to the rail so that the platform may be repositionable between the first end and the second end. The platform may have at least one front conveyance and at least one back conveyance. The platform may be movably coupled to the rail with the front conveyance(s) in contact with the front side of the rail and with the back conveyance (s) in contact with the back side of the rail. A clamp may be coupled to the platform, and the clamp may be configured to arrest a first portion of a conduit to the platform.

In further embodiments, the device may include a mounting mechanism having a fixed plate and a movable plate, and the movable plate may be movable towards and away from the fixed plate. A rail may be coupled to the mounting mechanism, the rail having a first end, a second end, an elongated front side, and an opposing elongated back side. A platform may be movably coupled to the rail so that the platform may be repositionable between the first end and the second end, and the platform may have one or more front conveyances and back conveyances. The platform may be movably coupled to the rail with a first front conveyance in contact with the front side of the rail and with a back conveyance in contact with the back side of the rail. A clamp may be coupled to the platform, and the clamp may be configured to arrest a first portion of a conduit to the platform.

In further embodiments, the device may include a second front conveyance, and the platform may be movably coupled to the rail with both the first front conveyance and the second front conveyance in contact with the front side of the rail and the back conveyance in contact with the back side of the rail.

In further embodiments, the device may include a mounting mechanism having movable plate base and a plate motivator, and the plate motivator may be movably coupled to the movable plate base via threading.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1:
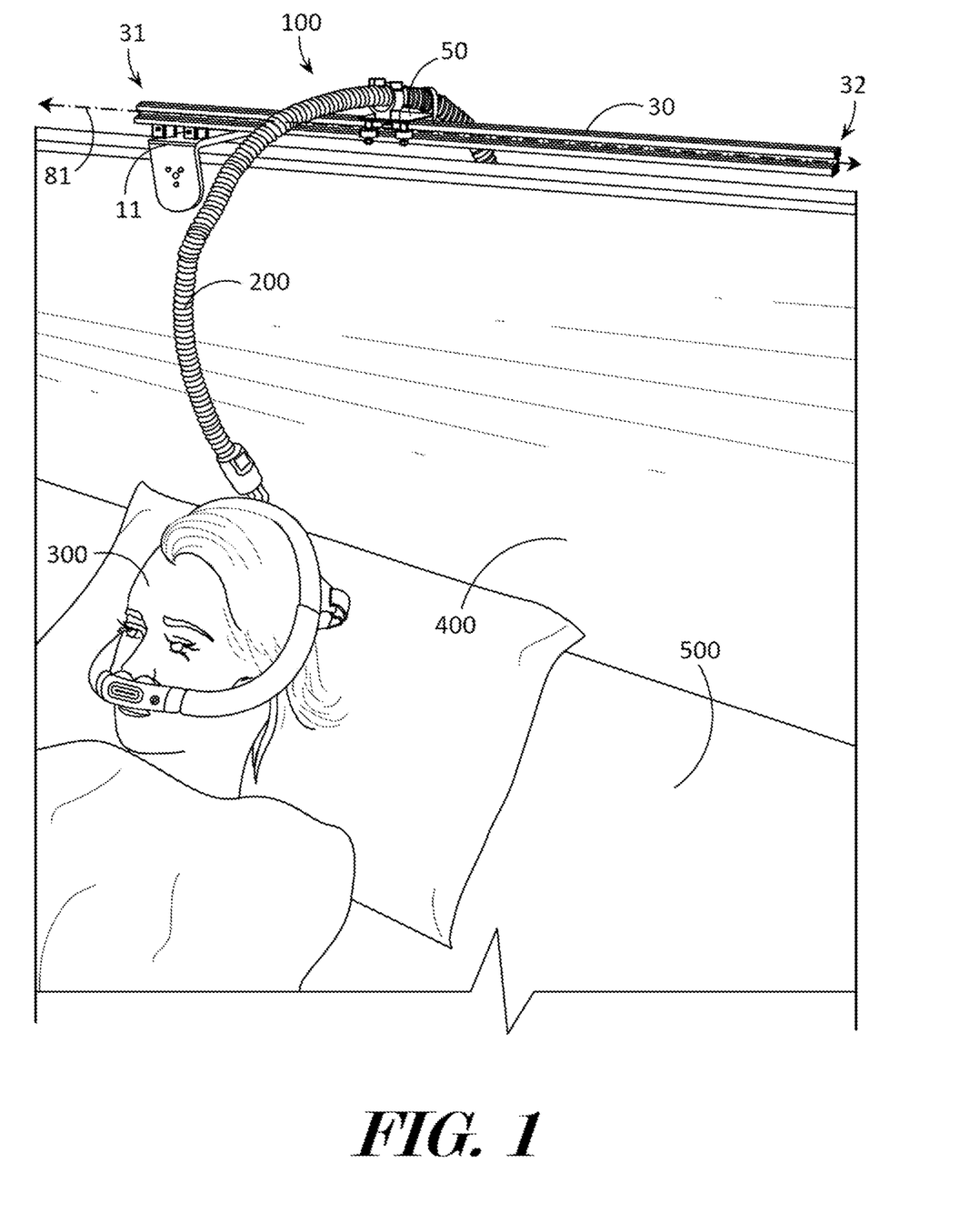
FIG. 1 depicts a front perspective view of an example of a conduit holding device coupled to a headboard and being used to support a conduit generally above the head of a user according to various embodiments described herein.
Figure 2:
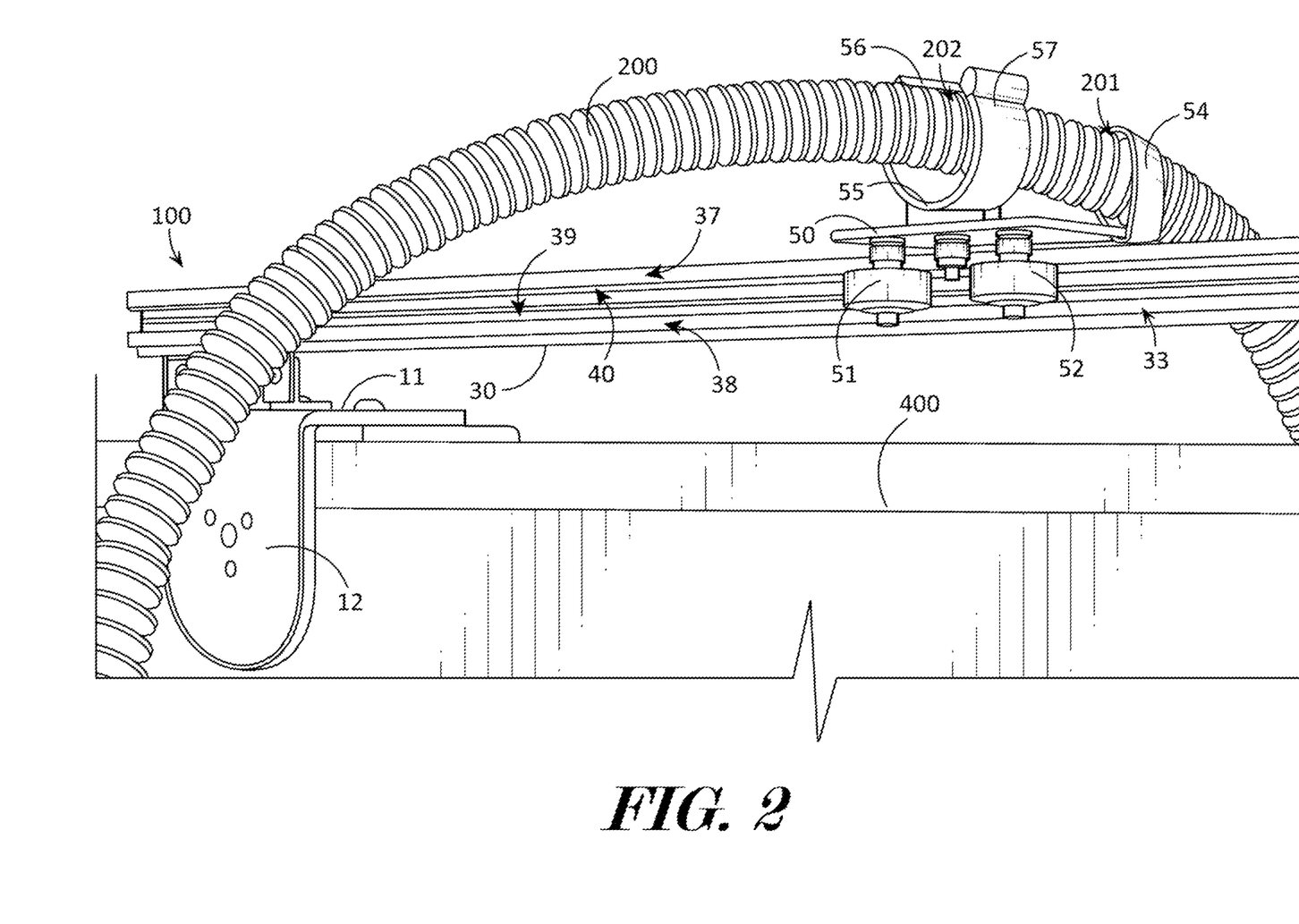
FIG. 2 illustrates a partial perspective view of an example of a conduit holding device according to various embodiments described herein.

For purposes of description herein, the terms "upper," "lower," "left," "right," "rear," "front," "top," "bottom", "side," "vertical," "horizontal," and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Although the terms "first," "second," etc. are used herein to describe various elements, these elements should not be limited by these terms. These terms are only used to distinguish one element from another element. For example, the first element may be designated as the second element, and the second element may be likewise designated as the first element without departing from the scope of the invention.

As used in this application, the term "about" or "approximately" refers to a range of values within plus or minus 10% of the specified number. Additionally, as used in this application, the term "substantially" means that the actual value is within about 10% of the actual desired value, more preferably within about 5% of the actual desired value and even more preferably within about 1% of the actual desired value of any variable, element or limit set forth herein.

A new conduit holding device is discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

Figure 3:
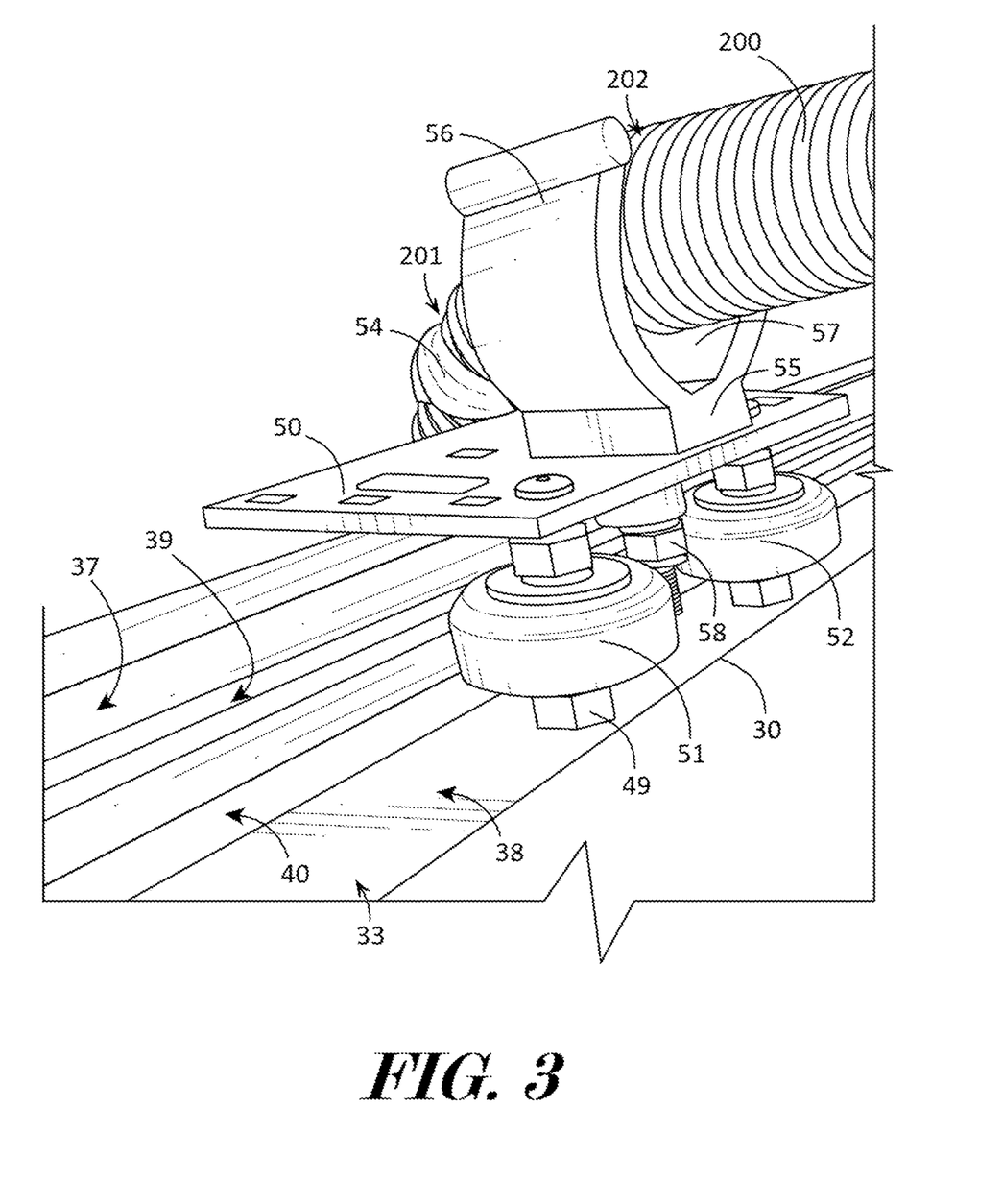
FIG. 3 shows a perspective view of an example of a platform of a conduit holding device according to various embodiments described herein.
Figure 4:
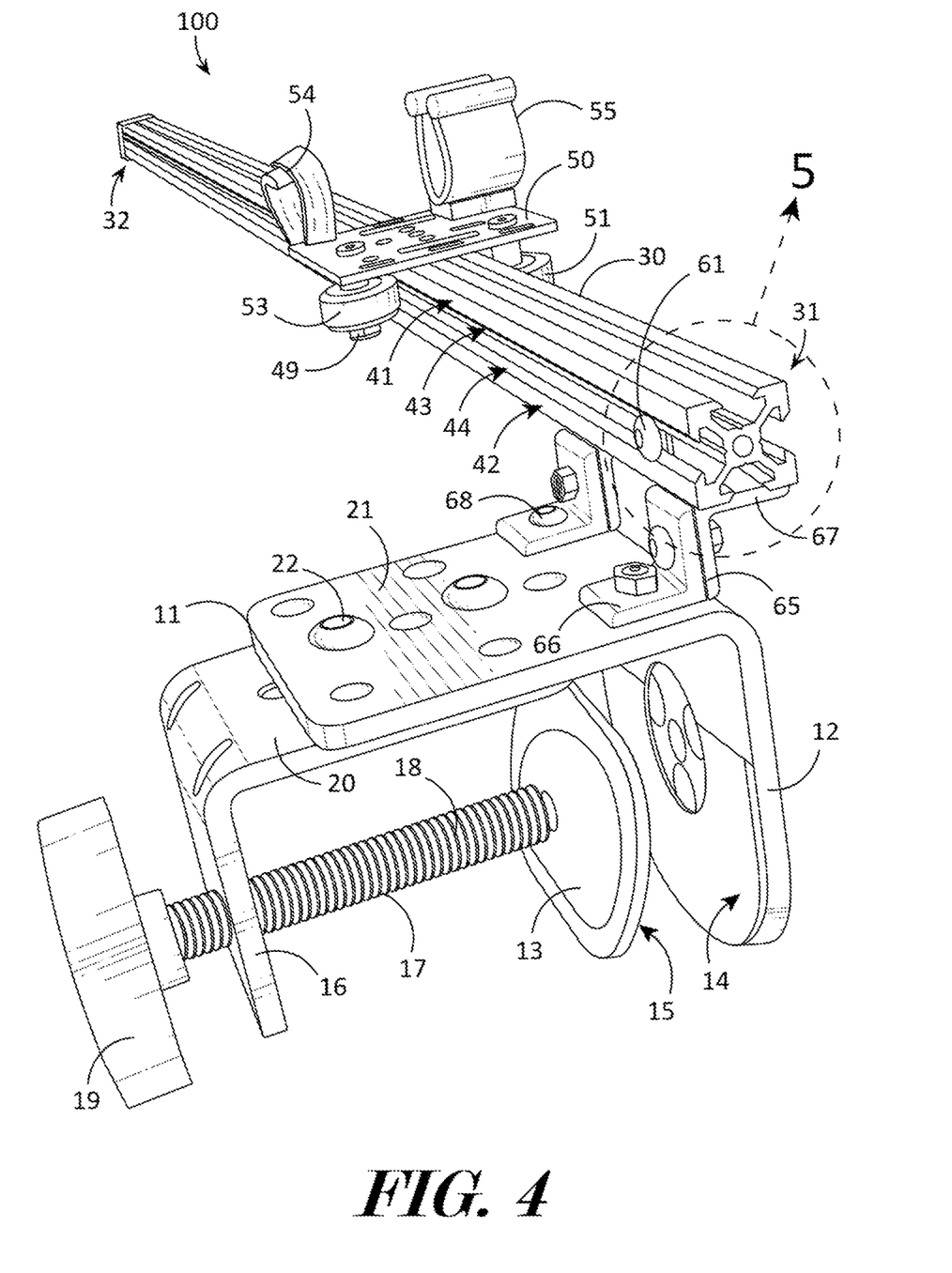
FIG. 4 depicts a rear perspective view of an example of a conduit holding device according to various embodiments described herein.
Figure 5:
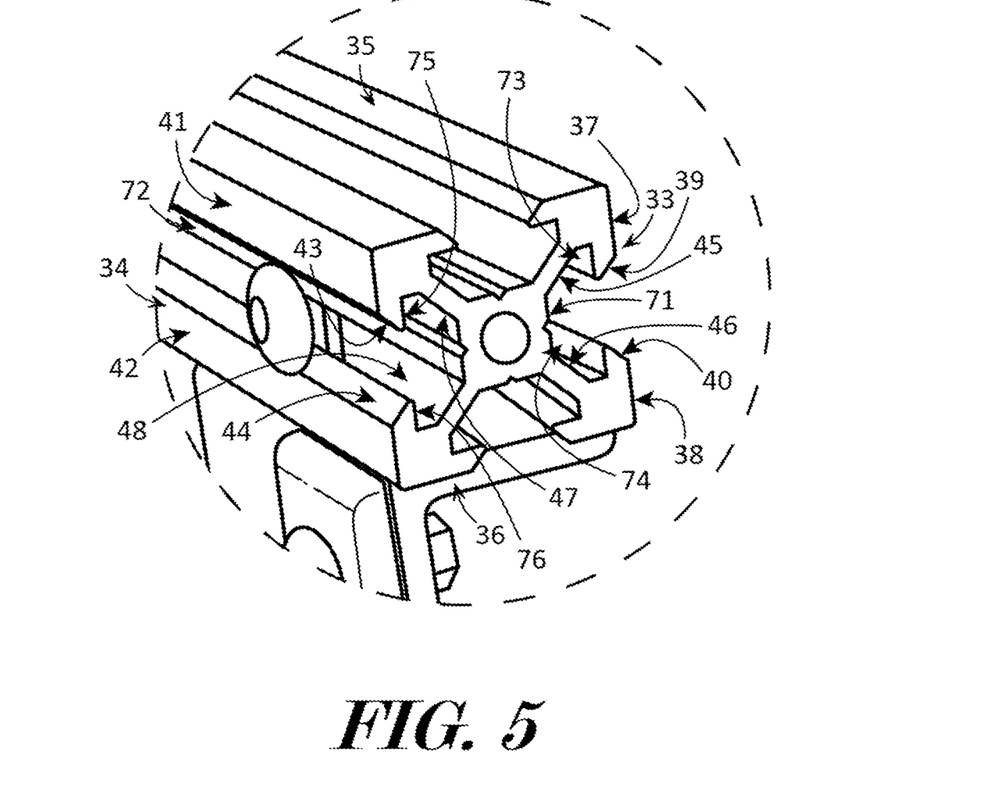
FIG. 5 illustrates an enlarged perspective view of the first end of the rail of the conduit holding device of FIG. 4 according to various embodiments described herein.
Figure 6:
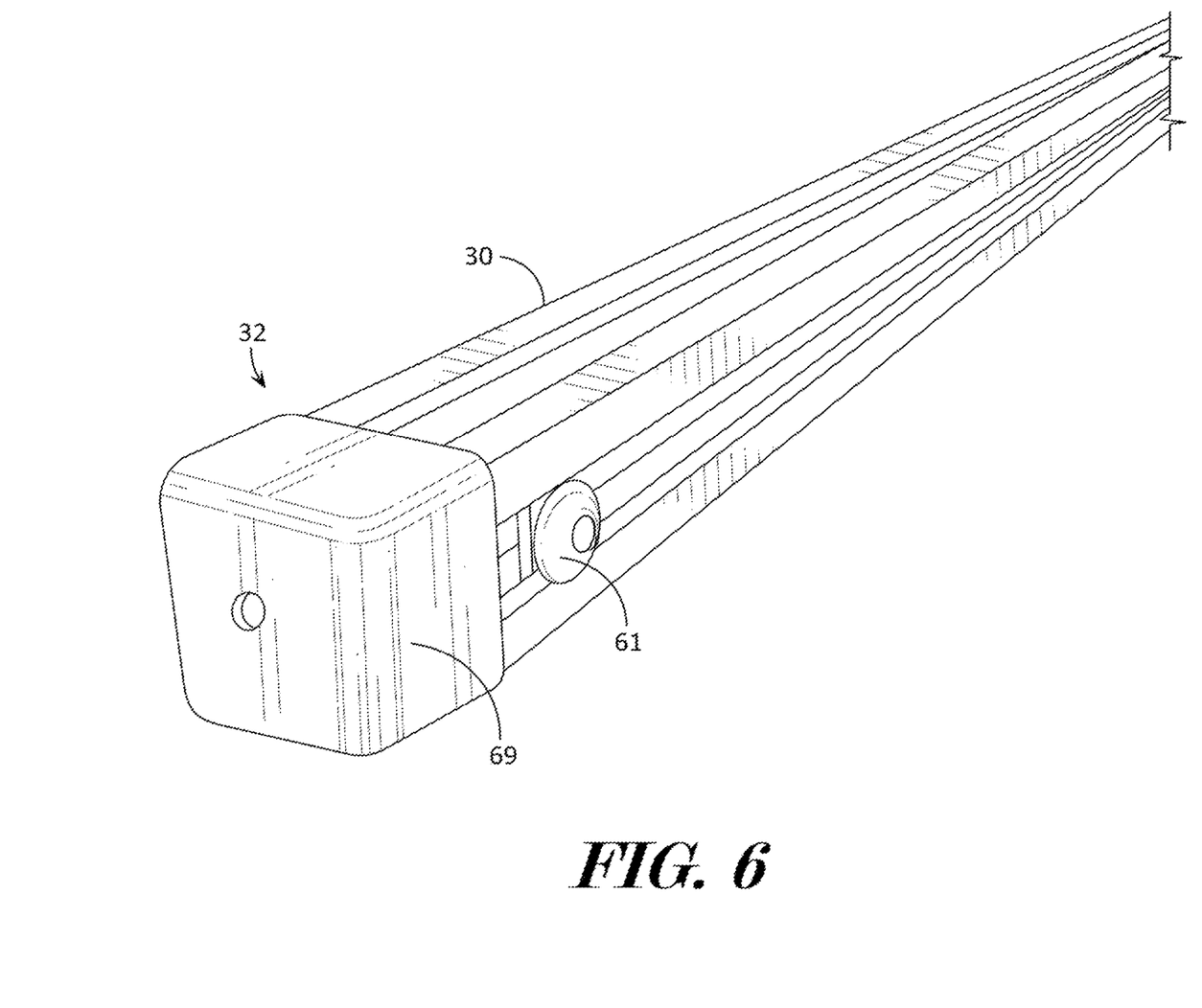
FIG. 6 shows a perspective view of a second end of an example rail of a conduit holding device according to various embodiments described herein.
Figure 7:
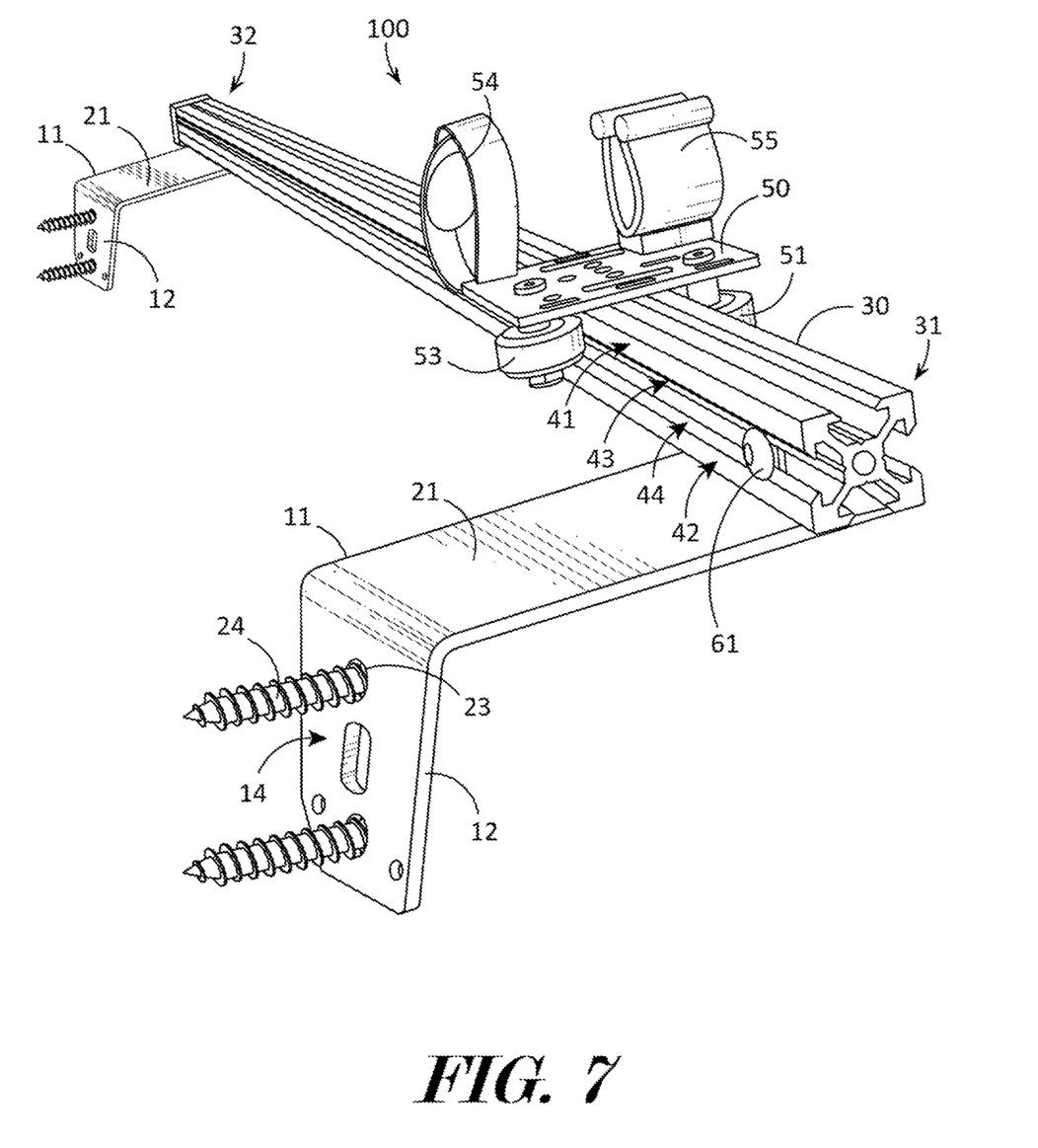
FIG. 7 depicts a rear perspective view of another example of a conduit holding device according to various embodiments described herein.

The present invention will now be described by example and through referencing the appended figures representing preferred and alternative embodiments. FIGS. 1, 4, and 7 perhaps best illustrate examples of a conduit holding device ("the device") 100 according to various embodiments. In some embodiments, and as shown in FIG. 7, the device 100 may include a rail 30 having a first end 31, a second end 32, an elongated front side 33, and an opposing elongated back side 34. A mounting mechanism 11 may be coupled to the rail 30, and the mounting mechanism 11 may have a fixed plate 12 and a fixed plate extension 21. The fixed plate extension 21 may couple the fixed plate 21 to the rail 30, and the fixed plate 12 may have one or more fastener apertures 23 which may be configured to receive a device fastener 24. The one or more device fasteners 24 may be used to couple the fixed plate 12 to an object, such as a wall, headboard, etc. A platform 50 may be movably coupled to the rail 30 so that the platform 50 may be repositionable between the first end 31 and the second end 32. The platform 50 may have at least one front conveyance 51, but preferably more than one front conveyance 51 as shown in FIG. 3, and at least one back conveyance 53. The platform 50 may be movably coupled to the rail 30 with the front conveyance(s) 51, 52, in contact with the front side 33 of the rail 30 and with the back conveyance(s) 53 in contact with the back side 34 of the rail 30. A clamp 54 may be coupled to the platform 51, and the clamp 54 may be configured to arrest a first portion of a conduit 201 to the platform 50. Preferably, the device 100 may be used to support a conduit 200, such as which may be used with a CPAP machine, generally above the head of a user 300 while allowing the supported portion of the conduit 200 to move back and forth in a lateral direction relative to the head of a user 300. In this manner the device 100 provides a greater range of conduit 200 movement than existing static tube holders alone can provide along with the additional benefit of the device 100 having a low vertical profile which provides a method for better concealment of CPAP tubing and a device 100 that is not large and cumbersome as existing devices.

In further embodiments, and as shown in FIGS. 1 and 4, the device 100 may comprise a mounting mechanism 11 having a fixed plate 12 and a movable plate 13, and the movable plate 13 may be movable towards and away from the fixed plate 12. A rail 30 may be coupled to the mounting mechanism 11, and the rail 30 may have a first end 31, a second end 32, an elongated front side 33, and an opposing elongated back side 34. A platform 50 may be movably coupled to the rail 30 so that the platform 50 may be repositionable between the first end 31 and the second end 32. The platform 50 may have one or more conveyances, such as a first front conveyance 51 and a back conveyance 53. Preferably, the platform 50 may be movably coupled to the rail 30 with the first front conveyance 51 in contact with the front side 33 of the rail 30 and with the back conveyance 53 in contact with the back side 34 of the rail 30. A clamp 54 may be coupled to the platform 50, and the clamp 54 may be configured to arrest a first portion 201 of a conduit 200 to the platform 50.

In some embodiments, the device 100 may comprise one or more mounting mechanisms 11 which may be used to removably couple the device 100 to objects and surfaces, such as to the headboard 400 of a bed 500, a wall, other furniture, etc. In some embodiments, and as shown in FIG. 7, a mounting mechanism 11 may include a fixed plate 12 which may be used to contact a wall, headboard 400 of a bed 500, or other object, and one or more device fasteners 24 may be used to couple the fixed plate 12 to the wall, headboard 400 of a bed 500, or other object. The fixed plate 12 may comprise one or more fixed surfaces 14 which may be configured to contact a portion of an object that the device 100 is to be coupled to. In further embodiments, a mounting mechanism 11 may include a fixed plate extension 21, and the fixed plate extension 21 may directly or indirectly couple the fixed plate 21 to the rail 30. In some embodiments, a fixed plate 12 and a fixed plate extension 21 may be generally planar in shape and coupled together so that they are angled between 25 and 75 degrees, and more preferably angled approximately 90 degrees, relative to each other. In further embodiments, a fixed plate 12 and a fixed plate extension 21 may be configured in any other shape and size.

In some embodiments, a fixed plate 12 may comprise one or more fastener apertures 23 which may be configured to receive a device fastener 24. A device fastener 24 may comprise a threaded screw, bolt, rivet, or any other coupling device or method. The one or more device fasteners 24 may be used to couple the fixed plate 12 to an object, such as a wall, headboard, etc.

In some embodiments, and as perhaps best shown in FIG. 4, a mounting mechanism 11 may also include a movable plate 13, and the movable plate 13 may be movable towards and away from the fixed plate 12 so as to enable objects and surfaces to be removably gripped or secured between the fixed plate 12 and movable plate 13. Similar to a fixed surface 14, a movable plate 13 may comprise one or more movable surfaces 15 which may be configured to contact a portion of an object that the device 100 is to be coupled to. Fixed plates 12 and fixed surfaces 14 along with movable plates 13 and movable surfaces 15 may be configured in any size and shape. Optionally, a fixed surface 14 and/or a movable surface 15 may comprise a non-marking cushion material, such as silicone foam, rubber, felt, etc., which may enable objects and surfaces to be gripped between the surfaces 14, 15, without damaging the objects and surfaces.

In some embodiments, a mounting mechanism 11 may comprise a movable plate base 16 and a plate motivator 17, and the plate motivator 17 may be movably coupled to the movable plate 16 base via threading 18. Preferably, a knob 19, lever, or other user manipulated interface may be operatively coupled to the plate motivator 17 so that by moving the knob 19, lever, etc., the plate motivator may also be moved thereby moving the movable plate 13 towards or away from the fixed plate 12. For example, by rotating the knob 19 in a first direction the plate motivator 17 and the movable plate 13 may be moved towards the fixed plate 12, via a threaded engagement between the plate motivator 17 and movable plate 16, and by rotating the knob 19 in a second direction the plate motivator 17 and the movable plate 13 may be moved aways from the fixed plate 12.

Optionally, a movable plate 13 may comprise a movable plate extension 20 and a fixed plate 12 may comprise a fixed plate extension 21, and the movable plate 13 and fixed plate 12 may be coupled together by coupling the movable plate extension 20 and fixed plate extension 21 via one or more mounting fasteners 22, welding, or any other suitable coupling method. In some embodiments, a movable plate 13 and a movable plate extension 20 may be generally planar in shape and coupled together so that they are angled between 25 and 75 degrees, and more preferably angled approximately 90 degrees, relative to each other. In further embodiments, a movable plate 13 and a movable plate extension 20 may be configured in any other shape and size.

The device 100 may comprise one or more rails 30 which may be coupled to the mounting mechanism 11. A rail 30 may be configured in any shape and size, and more preferably of an elongated shape and size so that its length dimension (along x-axis 81 shown in FIG. 1) may be greater than its width and height dimensions. In preferred embodiments, a rail 30 may have a first end 31, a second end 32, an elongated front side 33, and an opposing elongated back side 34, and the rail 30 may have an elongated shape so that the first end 31 and second end 32 may be separated by greater than 200 percent, and more preferably greater than 1,000 percent the distance that the elongated front side 33 and opposing elongated back side 34 may be separated.

A rail 30 may be coupled to the mounting mechanism 11 with any suitable coupling method, fastener, or device. In some embodiments, a device 100 may comprise one or more rail retainers 65 which may be used to couple the mounting mechanism 11 to a rail 30. Optionally, a rail retainer 65 may comprise one or more retainer brackets, such as a first retainer bracket 66 and a second retainer bracket 67, which may be coupled together and/or to the mounting mechanism 11 and rail 30 via one or more retainer fasteners 68. A rail retainer 65 and retainer brackets 66, 67, may be configured in any shape and size. Retainer fasteners 68 may comprise threaded fasteners, such as screws, nuts, and bolts, or any other fastening device or method.

A rail 30 may be configured in any elongated shape, such as an elongated, cylindrical shape, and elongated, rectangular prism shape, an elongated I-beam shape, etc., having an elongated front side 33 and an opposing or opposingly positioned elongated back side 34. Generally, a front side 33 may be substantially parallel to a back side 34, such that corresponding or like elements of the front side 33 may be substantially parallel to corresponding or like elements of the back side 34. As mentioned above, it should be understood that a front side 33 may be referred to as a "back side" and a back side 34 may be referred to as a "front side" depending on the orientation of the device 100 to a user or observer. The terms "front" and "back", as used herein are only used as differentiators, similar to the terms "first", "second", "third", etc., to aid in describing the invention.

In some embodiments, a front side 33 may comprise one or more front raised surfaces 37, 38, one or more front depressed surfaces 39, 40, one or more front lower surfaces 45, 46, a front bottom surface 71, and/or one or more front lip surfaces 73, 74. Likewise, a back side 34 may comprise one or more back raised surfaces 41, 42, one or more back depressed surfaces 43, 44, one or more back lower surfaces 47, 48, a back bottom surface 72, and/or back lip surfaces 75, 76. These surfaces 37-48, 71-76, may be elongated in shape so as to extend all or a portion of the distance between the ends 31, 32, of the rail 30.

Generally, a front depressed surface 39, 40 and back depressed surface 43, 44 may be depressed relative to the raised surfaces 37, 38, 41, 42, by the front depressed surfaces 39, 40, and back depressed surfaces 43, 44, being closer together to each other than the front raised surfaces 37, 38, may be to the back raised surfaces 41, 42. For example, a first front depressed surface 39 and a first back depressed surface 43 may be closer together than a first front raised surface 37 and a first back raised surface 41 are to each other.

Generally, front lower surfaces 45, 46, and back lower surfaces 47, 48, may be depressed relative to the depressed surfaces 39, 40, 43, 44, by the front lower surfaces 45, 46, and back lower surfaces 47, 48, being closer together to each other than the front depressed surfaces 39, 40, may be to the back depressed surfaces 43, 44. Likewise, bottom surfaces 71, 72, may be depressed relative to the lower surfaces 45, 46, 47, 48, by the front bottom surface 71 and back bottom surface 72 being closer together to each other than the front lower surfaces 45, 46, may be to the back lower surfaces 47, 48.

In preferred embodiments, a front side 33 may comprise a first front raised surface 37 and a second front raised surface 38, and the first front raised surface 37 and second front raised surface 38 may be separated by a first front depressed surface 39 and/or second front depressed surface 40. Likewise, a back side 34 may comprise a first back raised surface 41 and a second back raised surface 42, and the first back raised surface 41 and second back raised surface 42 may be separated by a first back depressed surface 43 and/or second back depressed surface 44.

Optionally, a front side 33 may comprise a front bottom surface 71 and a back side 34 may comprise a back bottom surface 72, and the first front depressed surface 39 and second front depressed surface 40 (and therefore the first front raised surface 37 and second front raised surface 38) may be separated by the front bottom surface 71 while the first back depressed surface 43 and second back depressed surface 44 (and therefore the first back raised surface 41 and second back raised surface 42) may be separated by the back bottom surface 72.

Optionally, a front side 33 may comprise one or more front lip surfaces 73, 74, and a back side 34 may comprise one or more back lip surfaces 75, 76. Preferably, front lip surfaces 73, 74, may be approximately parallel to front raised surfaces 37, 38, and back lip surfaces 75, 76, may be approximately parallel to back raised surfaces 41, 42. Preferably, front lip surfaces 73, 74, and back lip surfaces 75, 76, may be closer to each other than the front raised surfaces 37, 38, are to the back raised surfaces 41, 42, and also closer together than the front depressed surfaces 39, 40, are to the back depressed surfaces 43, 44.

The device 100 may comprise a platform 50 that may be movably coupled to the rail 30 so that the platform 50 may be repositionable along all or a portion of the rail 30 between the first end 31 and the second end 32. A platform 50 that may be movably coupled to the rail 30 so that the platform 50 may move back and forth along all or a portion of the rail in a lateral direction (along an x-axis 81 as shown in FIG. 1).

In some embodiments, the device 100 may comprise one or more conveyances, 51, 52, 53, which may be used to movably couple the platform 50 to the rail 30 and to decrease friction as the platform 50 moves along the rail 30. In preferred embodiments, a conveyance 51, 52, 53, may comprise a wheel, such as a polyurethane wheel, urethane wheel, metal wheel, etc., while in further embodiments, a conveyance 51, 52, 53, may comprise a caster, bearing, tread or track, low friction pad or bumper, low friction plate, or any other suitable device configured to reduce the friction between the rail 30 and platform 50. In further preferred embodiments, a conveyance 51, 52, 53, may comprise a wheel that may be rotatably coupled to the platform 50 so that the conveyances 51, 52, 53, may be configured to contact one or more surfaces 37-48, 71-76, of the rail 30. One or more conveyance fasteners 49 or any other suitable coupling device or method may be used to couple a conveyance 51, 52, 53, to the platform 50.

In some embodiments, the device 100 may comprise one or more conveyances, 51, 52, 53, which may be used to movably couple the platform 50 to the rail 30 with one or more of the conveyances, 51, 52, 53, in contact with one or more surfaces 37-48, 71-76, of the front side 33 and/or back side 34. In preferred embodiments, the device 100 may comprise one or more, and more preferably two, front conveyances 51, 52, which may contact one or more front surfaces 37-40, 45, 46, 71, 73, 74, of the front side 33 and one or more back conveyances 53 which may contact one or more back surfaces 41-44, 47, 48, 72, 75, 76, of the back side 34. In further preferred embodiments, the device 100 may comprise a first 51 and second 52 front conveyance that may be configured to contact one or more front depressed surfaces 39, 40, and a back conveyance 53 that may be configured to contact one or more back depressed surfaces 43, 44. In further embodiments, the device 100 may comprise a first 51 and second 52 front conveyance that may be configured to contact one or more front raised surfaces 37, 38, and a back conveyance 53 that may be configured to contact one or more back raised surfaces 41, 42.

In some embodiments, the device 100 may comprise one or more rail stops 61 which may be coupled at one or more locations on a rail 30 and which may be used to limit the distance that a platform 50 may move along a rail or locations that a platform may be located at along a rail 30. In some embodiments, a rail stop 61 may comprise or may form a protrusion or obstacle that extends above one or more surfaces 37-48, 71, 72, of a front side 33 and/or back side 34 to which the rail stop 61 may be coupled so that the rail stop 61 may prevent movement of a conveyance 51, 52, 53, past the rail stop. In this manner, a rail stop 61 may prevent the platform 50 from being positioned between the rail stop 61 and one of the first end 31 and second end 32 of the rail 30. For example, a rail stop 61 may be coupled to a back side 34 of a rail 30, such that the rail stop removably grips the back lower surfaces 47, 48, and back raised surfaces 41, 42, and by extending above the back raised surfaces 41, 42, the rail stop 61 may block movement of a back conveyance 53 past the rail stop 61. In some embodiments, a rail stop 61 may comprise a threaded fastener which may be tightened against another fastener to grip one or more surfaces 37-48, 71, 72, of a rail 30, thereby coupling the rail stop 61 to the rail 30. For example, a rail stop 61 may be coupled to the back side 34 by being configured to grip two or more of the back raised surfaces 41, 42, back depressed surfaces 43, 44, and back lip surfaces 75, 76. In further embodiments, a rail stop 61 may comprise an adhesive fastener, a magnetic fastener, or any other device having a size or shape that a conveyance 51, 52, 53, may be unable to move past and that may be coupled, and more preferably removably coupled, to a rail 30.

In some embodiments, the device 100 may comprise a clamp 54 that may be coupled to the platform 50, and the clamp 54 may be configured to arrest a first portion 201 of a conduit 200 to the platform 50. Generally, a clamp 54 may be used to couple, and more preferably removably couple, a portion 201 of a conduit 200 to the platform 50 so that the conduit 200 portion 201 may be prevented from moving relative to the platform 50. In preferred embodiments, a clamp 54 may comprise a hook and loop fastener which may be configured to wrap around and grip a conduit 200 portion 201. In further embodiments, a clamp 54 may comprise a hose clamp, cable tie, or any other device or method which may be used to arrest a first portion 201 of a conduit 200 to the platform 50. Any suitable coupling method may be used to couple a clamp 54 to a platform 50. As an example, a clamp 54 may comprise a hook and loop fastener which may be inserted through a slot or aperture on the platform 50 and which may wrap around and grip a conduit 200 portion 201 and attach back to itself.

In some embodiments, the device 100 may comprise a clasp 55 that may be coupled to the platform 50, and the clasp 55 may be configured to repositionably secure a second portion 202 of a conduit 200 to the platform 50.

Generally, a clasp 55 may be used to repositionably secure a portion 202 of a conduit 200 to the platform 50 so that the conduit 200 portion 202 may be prevented from moving in at least one direction relative to the platform 50. For example, a clasp 55 may comprise a first clasp arm 56 and a second clasp arm 57, and the clasp 55 may be configured to receive a second portion 202 of the conduit 200 by positioning the second portion 202 of the conduit 200 between the clasp arms 56, 57, to enable the conduit portion 202 to slide between the clasp arms 56, 57, while gripping the conduit portion 202 between the clasp arms 56, 57, to prevent side to side motion. In further embodiments, a clamp 54 may comprise a hose clamp, cable tie, or any other device or method which may be used to prevent a conduit portion 202 from moving in at least one direction relative to the platform 50. A clasp 55 may be coupled to a platform 50 via one or more clasp fasteners 58, optionally comprising screws, bolts, nuts, or other threaded fasteners, or with any other suitable coupling device or method.

In some embodiments, the device 100 may comprise a rail cap 69 which may cover an end 31, 32, of the rail 30. Preferably, a rail cap 69 may provide a protective cover for any sharp edges on an end 31, 32, of the rail 30. Optionally, a rail cap 69 may function as a rail stop 61 so as to prevent a platform 50 from sliding off an end 31, 32, of the rail 30. A rail cap 69 may be made from or may comprise a soft flexible plastic or any other suitable material.

While some exemplary shapes and sizes have been provided for elements of the device 100, it should be understood to one of ordinary skill in the art that the mounting mechanism 11, rail 30, platform 50, and any other element described herein may be configured in a plurality of sizes and shapes including "T" shaped, "X" shaped, square shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

Additionally, while some materials have been provided, in other embodiments, the elements that comprise the device 100 may be made from or may comprise durable materials such as aluminum, steel, other metals and metal alloys, wood, hard rubbers, hard plastics, fiber reinforced plastics, carbon fiber, fiberglass, resins, polymers or any other suitable materials including combinations of materials. Additionally, one or more elements may be made from or may comprise durable and slightly flexible materials such as soft plastics, silicone, soft rubbers, or any other suitable materials including combinations of materials. In some embodiments, one or more of the elements that comprise the device 100 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the device 100 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, a slide-to-lock type connection method or any other suitable temporary connection method as one reasonably skilled in the art could envision to serve the same function. In further embodiments, one or more of the elements that comprise the device 100 may be coupled by being one of connected to and integrally formed with another element of the device 100.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A conduit holding device, the device comprising:
   a mounting mechanism having a fixed plate and a movable plate, the movable plate movable towards and away from the fixed plate;
   a rail coupled to the mounting mechanism, the rail having a first end, a second end, an elongated front side, and an opposing elongated back side;
   a platform movably coupled to the rail so that the platform may be repositionable between the first end and the second end, the platform having a first front conveyance and a back conveyance, wherein the platform is movably coupled to the rail with the first front conveyance in contact with the front side of the rail and with the back conveyance in contact with the back side of the rail; and
   a clamp coupled to the platform, the clamp configured to arrest a first portion of a conduit to the platform.

2. The device of claim 1, wherein the first front conveyance comprises a first wheel that is rotatably coupled to platform, and wherein the back conveyance comprises a second wheel that is rotatably coupled to platform.

3. The device of claim 1, wherein the clamp comprises a hook and loop fastener.

4. The device of claim 1, further comprising a clasp that is configured to receive a second portion of the conduit.

5. The device of claim 4, wherein the clasp comprises a first clasp arm and a second clasp arm, and wherein the clasp is configured to receive the second portion of the conduit by positioning the second portion of the conduit between the first clasp arm and second clasp arm.

6. The device of claim 1, further comprising a rail stop coupled to the rail, wherein the rail stop prevents the platform from being positioned between the rail stop and one of the first end and second end.

7. The device of claim 1, further comprising a second front conveyance, wherein the platform is movably coupled to the rail with both the first front conveyance and the second front conveyance in contact with the front side of the rail and the back conveyance in contact with the back side of the rail.

8. The device of claim 1, wherein the front side of the rail comprises a first front raised surface and a front depressed surface, wherein the back side of the rail comprises a back raised surface and a back depressed surface, wherein the front depressed surface and back depressed surface are closer together than the first front raised surface and back raised surface, wherein the first front conveyance is configured to contact the front depressed surface, and wherein the back conveyance is configured to contact the back depressed surface.

9. The device of claim 8, further comprising a second front raised surface, wherein the first front raised surface and second front raised surface are separated by the front depressed surface.

10. The device of claim 1, wherein the mounting mechanism comprises a movable plate base and a plate motivator, and wherein the plate motivator is movably coupled to the movable plate base via threading.

11. The device of claim 10, further comprising a knob that is coupled to the plate motivator.

12. A conduit holding device, the device comprising:
- a rail having a first end, a second end, an elongated front side, and an opposing elongated back side;
- a mounting mechanism having a fixed plate and a fixed plate extension, the fixed plate extension coupling the fixed plate to the rail, and the fixed plate having a fastener aperture;
- a platform movably coupled to the rail so that the platform may be repositionable between the first end and the second end, the platform having a first front conveyance and a back conveyance, wherein the platform is movably coupled to the rail with the first front conveyance in contact with the front side of the rail and with the back conveyance in contact with the back side of the rail; and
- a clamp coupled to the platform, the clamp configured to arrest a first portion of a conduit to the platform.

13. The device of claim 12, wherein the first front conveyance comprises a first wheel that is rotatably coupled to platform, and wherein the back conveyance comprises a second wheel that is rotatably coupled to platform.

14. The device of claim 12, wherein the clamp comprises a hook and loop fastener.

15. The device of claim 12, further comprising a clasp that is configured to receive a second portion of the conduit.

16. The device of claim 15, wherein the clasp comprises a first clasp arm and a second clasp arm, and wherein the clasp is configured to receive the second portion of the conduit by positioning the second portion of the conduit between the first clasp arm and second clasp arm.

17. The device of claim 12, further comprising a rail stop coupled to the rail, wherein the rail stop prevents the platform from being positioned between the rail stop and one of the first end and second end.

18. The device of claim 12, further comprising a second front conveyance, wherein the platform is movably coupled to the rail with both the first front conveyance and the second front conveyance in contact with the front side of the rail and the back conveyance in contact with the back side of the rail.

19. The device of claim 12, wherein the front side of the rail comprises a first front raised surface and a front depressed surface, wherein the back side of the rail comprises a back raised surface and a back depressed surface, wherein the front depressed surface and back depressed surface are closer together than the first front raised surface and back raised surface, wherein the first front conveyance is configured to contact the front depressed surface, and wherein the back conveyance is configured to contact the back depressed surface.

20. The device of claim 19, further comprising a second front raised surface, wherein the first front raised surface and second front raised surface are separated by the front depressed surface.

* * * * *